United States Patent [19]

Dawson et al.

[11] Patent Number: 4,913,878
[45] Date of Patent: Apr. 3, 1990

[54] METHOD OF TESTING THE MAGNESIUM CONTENT OF MAGNESIUM-TREATED CAST IRON

[75] Inventors: John V. Dawson, Wilmcote Nr. Stratford-Upon-Avon; Peter White, Redditch, both of England

[73] Assignee: General Signal Corporation, Stamford, Conn.

[21] Appl. No.: 301,569

[22] Filed: Jan. 24, 1989

[30] Foreign Application Priority Data

Feb. 5, 1988 [GB] United Kingdom ............... 8802619

[51] Int. Cl.[4] .............................................. C22C 33/00
[52] U.S. Cl. ...................................... 420/18; 420/129
[58] Field of Search ................................... 420/18, 129

[56] References Cited

U.S. PATENT DOCUMENTS

| | | | |
|---|---|---|---|
| 2,250,489 | 7/1960 | Lorig et al. | 420/129 |
| 2,527,037 | 10/1950 | Smalley | 420/18 |
| 2,933,385 | 4/1960 | Moore | 420/129 |
| 3,546,921 | 12/1970 | Bourke et al. | 420/129 |
| 4,059,996 | 11/1977 | Cure | 420/129 |
| 4,166,738 | 9/1979 | Plessers | 420/129 |
| 4,261,740 | 4/1981 | Plessers | 420/129 |
| 4,358,948 | 11/1982 | Plessers | 420/18 |
| 4,570,496 | 1/1986 | Falk | 420/129 |

*Primary Examiner*—Peter D. Rosenberg
*Attorney, Agent, or Firm*—Robert R. Hubbard

[57] ABSTRACT

In the manufacture of ductile iron it is important to know that the magnesium content is above (or possibly below) a threshold value. It is known that the presence of magnesium prevents tellurium causing solidification of a sample with carbidic eutectic arrest. Accordingly we treat a sample in a receptacle with a known quantity of sulphur (or selenium) such as just to neutralize the threshold quantity of magnesium, then we observe whether, on solidification, the eutectic arrest is graphitic (indicating that more than the threshold quantity of magnesium is present) or carbidic, indicating less magnesium. The observation is most simply done (and can be done semi-automatically) by timing a cooling curve between two predetermined temperatures.

9 Claims, 5 Drawing Sheets

METHOD OF TESTING THE MAGNESIUM CONTENT OF MAGNESIUM-TREATED CAST IRON

One of the most important high strength types of cast iron, known as ductile, nodular or SG iron, is produced by adding magnesium to liquid cast iron to produce a retained magnesium content of about 0.04 per cent or more. When this amount of magnesium is retained the iron solidifies with nodular or spherical graphite which causes the iron to have greatly increased strength and a considerable amount of elongation, for which reason it is now generally known as ductile iron. The magnesium is added in the foundry to liquid cast iron in the ladle or in a special-purpose treatment vessel, using a wide range of treatment materials including pure magnesium or alloys based upon ferrosilicon or nickel and containing magnesium contents ranging from about 16 per cent down to about 3 per cent. The amount of magnesium retained in the iron depends upon the proportion of the added magnesium which has dissolved. Some of the magnesium added is lost by combination with oxygen in the atmosphere and some is lost because it combines with the sulphur in the iron to be treated. Both magnesium sulphide and magnesium oxide are formed during treatment and are removed as slag which usually floats to the surface of the iron.

Depending upon the composition of the iron before treatment and many other details of the treatment process, well understood by foundrymen, the lowest magnesium content at which nodular or spheroidal graphite will be obtained may be below 0.04 per cent and, in certain cases, may be as low as 0.03 per cent. However, for practical purposes it is usual to aim to achieve a minimum retained magnesium content of 0.04 per cent although the test to which the present application refers can be adjusted to match differing requirements for the critical magnesium content. In some cases it may be important also to limit the upper level of magnesium content retained, both for purposes of economy of magnesium addition, and also because a high magnesium content may promote various kinds of defects including dross defects. In the manufacture of nodular iron, therefore, it is very important to be able to exercise accurate control over the magnesium content achieved after treatment, in order to avoid pouring metal to form castings if it is not of the right composition. If insufficient magnesium has been added and if this can be ascertained quickly enough, there will often be an opportunity of making a further addition before the iron is cast into moulds.

At the present time the only methods of judging the magnesium content are either by casting a very small sample which can be examined metallographically to verify that its graphite structure is correct, or by carrying out rapid chemical or spectroscopic analysis, which involves casting a sample which must be solidified and then transferred to a laboratory. Both of these processes are time-consuming and do not usually permit of any corrective treatment if the composition of the metal is incorrect.

Other important aspects of composition of nodular iron which are controlled on the shopfloor are the carbon, silicon and carbon equivalent contents of the iron. These can be determined by thermal analysis of small samples of liquid metal prior to magnesium treatment poured into small expendable sand cups which contain a thermocouple. Untreated liquid iron suitable for producing nodular iron will normally solidify with a graphitic structure in such a cup and produce a cooling curve of the shape shown in FIG. 1 of the accompanying drawings. The first discontinuity in the curve is the liquidus temperature at which dendrites of austenite first form in the mould. The second major discontinuity occurs at the eutectic temperature range in which the bulk of the solidification, including graphite formation, takes place. The temperature of the liquidus is directly related to the carbon equivalent (liquidus), which is a well-established combined measure of the carbon and silicon contents. The temperature of the graphitic eutectic arrest is not usually measured. It is well known that if the thermal analysis sample cup contains sufficient of a substance including free tellurium, then the eutectic solidification of the iron sample before magnesium treatment is changed from graphitic to carbidic. When this happens the cooling curve assumes a different form and the second discontinuity takes place at a lower temperature as shown in FIG. 2. When this occurs the temperature of the eutectic arrest may be measured and used, together with that of the liquidus arrest to calculate the carbon and silicon contents of the iron.

The object of the present invention is to extend the principle of thermal analysis in an entirely novel way to make it possible to use a thermal analysis technique not for the known purpose of obtaining a measure of the carbon equivalent content but for the purpose of testing the magnesium content of the iron when it has been treated with magnesium.

It has been known for some time that the use of tellurium in a thermal analysis sample to achieve carbidic eutectic solidification for the purpose of measuring carbon and silicon cannot be applied to magnesium-containing irons since, in the presence of magnesium, tellurium cannot prevent the iron from solidifying with a graphitic eutectic structure. U.S. Pat. Specification No. 4 166738 showed that if sufficient sulphur or selenium can also be added to the thermal analysis sample to neutralise completely any magnesium which may be present, then tellurium again becomes effective in achieving carbidic eutectic solidification, since once the magnesium is neutralised the iron behaves as though it had not been treated with magnesium.

We have discovered that by taking advantage of the known effects of tellurium and sulphur or selenium in a thermal analysis cup and making a determination during solidification, we can provide a new kind of test which will determine whether sufficient magnesium has been retained for the purpose of making nodular iron.

According to the present invention there is provided a method of testing the actual magnesium content of magnesium-treated iron in which a molten sample of magnesium-treated iron is introduced into a receptacle containing additives of tellurium and either sulphur or selenium and allowed to cool and solidify, the amounts of tellurium and sulphur or selenium being controlled measured quantities, the quantity in the case of sulphur or selenium being such that the addition is just sufficient to neutralise completely a predetermined threshold percentage (desired content) of magnesium, and then observing whether the cooling behaviour results in graphitic or carbidic eutectic arrest.

If the solidified iron on eutectic arrest is carbidic, this indicates that all the magnesium was neutralised by the sulphur or selenium, so it must have been below the threshold percentage. If the structure is graphitic, there must still be some magnesium present, so it was (before neutralisation) above the threshold value. Sulphur is preferred because it is believed to be more effective than selenium which, in any event, is a poisonous and unpleasant substance.

The reference percentage of magnesium may be determined from a relationship evaluated from measurements of the amounts of sulphur needed to neutralise various quantities of magnesium in the iron.

The predetermined reference percentage preferably corresponds to a desired minimum magnesium content for the iron. Thus when the molten sample of iron contains less than the desired minimum magnesium content, all of the magnesium will be neutralised by the measured quantity of sulphur and sufficient tellurium will remain to promote carbidic eutectic solidification, but when the sample contains more than the desired magnesium content, all of the sulphur and tellurium will combine with magnesium and graphitic eutectic solidification will take place, indicating that sufficient magnesium has been added to the iron.

Alternatively, the reference level may correspond to a desired maximum magnesium content for the iron, in which case graphitic eutectic solidification will indicate that too much magnesium has been added to the iron.

The best way of detecting whether the structure is carbidic or graphitic is by observing the cooling behaviour of the sample through the eutectic temperature.

Preferably, the receptacle containing the measured quantity of tellurium and the measured quantity of sulphur is a thermal analysis cup in which a time measurement may be made during cooling of the molten sample to determine whether the sample undergoes graphitic eutectic or carbidic eutectic solidification. It is particularly convenient to measure the time taken for the sample to cool from one predetermined temperature level to another predetermined temperature level. In this case, with a suitable choice of the temperature levels, a relatively long cooling time indicates graphitic eutectic solidification and a relatively short cooling time indicates either carbidic eutectic solidification or a mixture of carbidic and graphitic eutectic solidification producing a 'mottled' structure.

This time measurement is particularly advantageous when the reference level corresponds to a desired minimum magnesium content since the relatively short cooling time not only indicates that the sample contains insufficient magnesium but also enables more magnesium to be added to the molten iron from which the sample was taken.

A method in accordance with the invention will now be described with reference to the accompanying drawings, in which:

FIGS. 1 and 2, which have already been referred to above, are both temperature-time cooling curves, FIG. 1 showing the curve for a melt which solidifies with a graphitic structure and FIG. 2 showing a curve for a melt that solidifies with a carbidic structure;

A thermal analysis cup 1 (FIG. 5) is coated internally with a tellurium-containing coating which contains sufficient tellurium to cause any non-magnesium-containing iron to solidify with a carbidic structure. This usually requires the coating to contain enough tellurium to constitute about 0.1 to 0.4 per cent of the weight of the iron cast into the thermal analysis sample.

Figure 1:
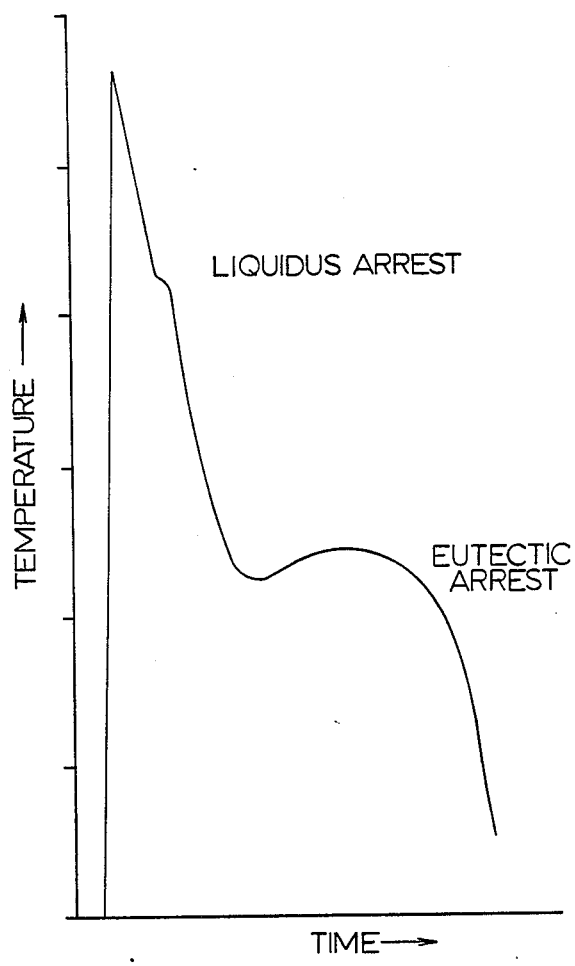
Figure 2:
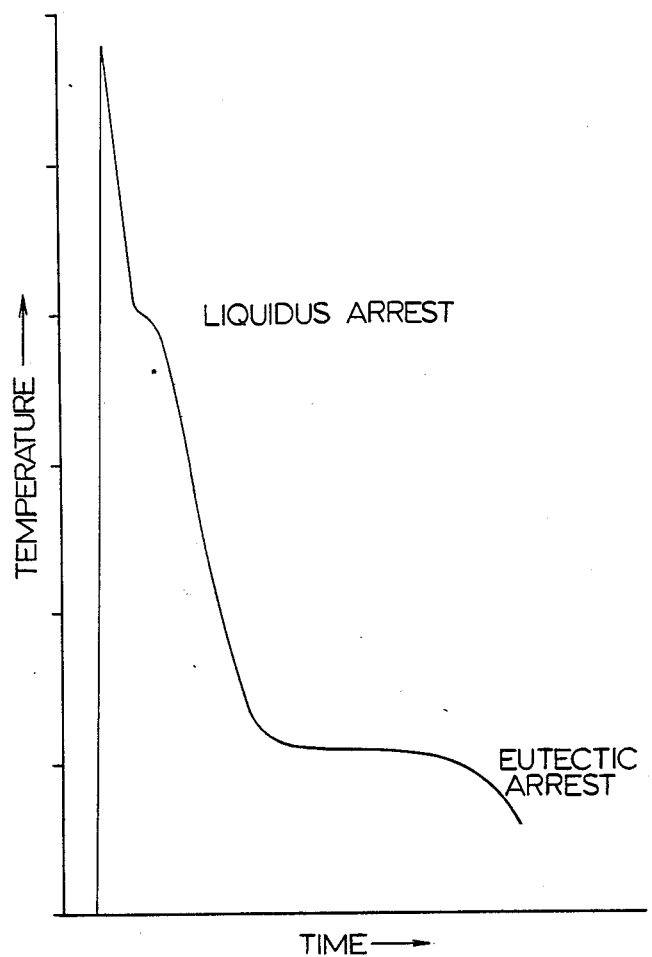
Figure 3:
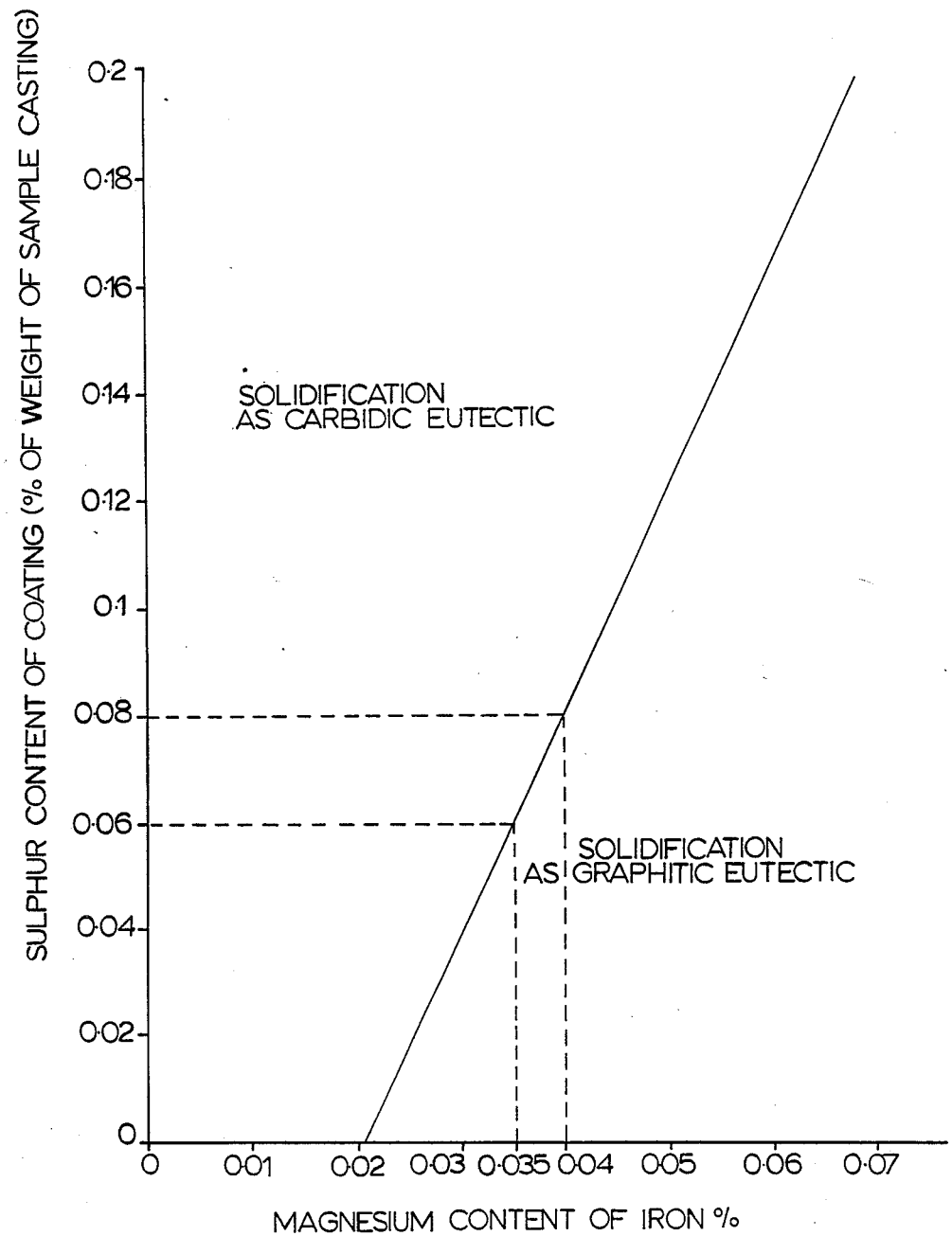
FIG. 3 is a graph showing the relationship between the sulphur content of the coating of the sample cup and the magnesium content of the iron.

An addition of elemental sulphur is then made to the thermal analysis cup, either as a coating or as a discrete particle which contains a known amount of sulphur found to be sufficient to neutralise an amount of magnesium which would be just too low to produce the desired nodular graphite structure. This amount cannot be calculated but has been determined from measurements relating the magnesium content of the iron to the sulphur content contained in the cup, expressed as a percentage of the weight of the iron. FIG. 3 illustrates the relationship which we have determined. Thus, if the desired minimum retained content of magnesium is 0.04 per cent, then the sulphur content of the cup must be 0.08 per cent of the weight of the iron, and if the desired minimum magnesium content is 0.035 per cent, then the sulphur content must be 0.06 per cent of the weight of the iron.

Although we have referred above to the addition of elemental sulphur, it should be understood that, within the scope of the invention, the sulphur or selenium could be added in the form of a compound, for example iron sulphide or iron selenide, and when dissolved it will yield the sulphur or selenium in elemental form.

Figure 5:
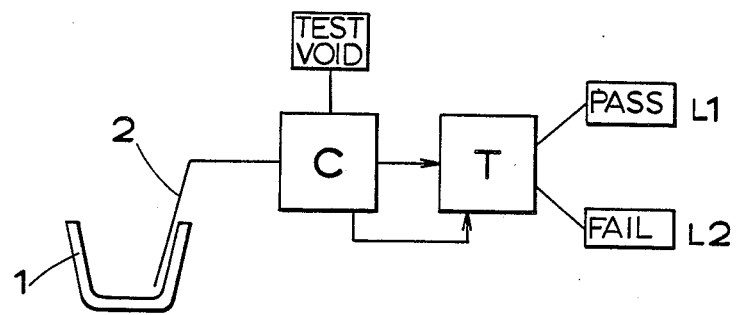
FIG. 5 shows diagrammatically a form of apparatus suitable for putting the invention into practice.

To carry out the test a sample of molten iron is poured into the thermal analysis cup prepared according to the above rules at a temperature of not less than 1310° C. This is to ensure a sufficiently high temperature of metal in the thermal analysis cup for the cooling conditions to become settled before any measurements are made. A thermocouple temperature-sensing device 2 in the cup 1 produces an e.m.f. which is fed to control equipment C (FIG. 5). If the initial temperature in the cup after pouring of the sample fails to reach, say, 1200° C., then this is detected by the equipment C, which automatically indicates an invalid test, for example by lighting up a lamp 3 bearing the legend 'TEST VOID'.

The control equipment C is designed to measure and record the time which the sample in the cup 1 takes to cool between two fixed temperatures on the cooling curve. These temperatures are 1170° C. and 1135° C. and are illustrated in FIG. 4 on three types of cooling curve which might be obtained.

Figure 4:
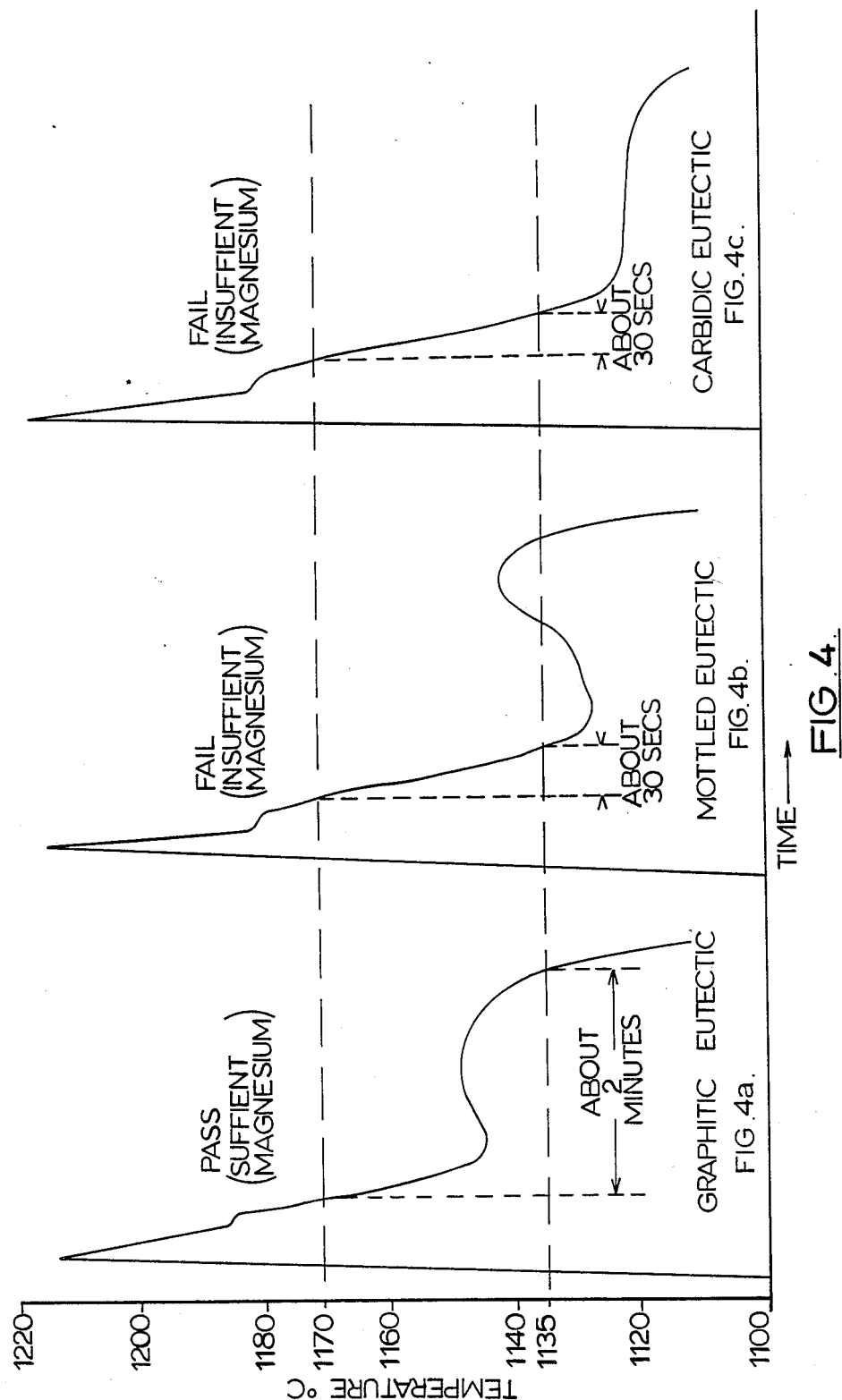
FIG. 4 shows a series of temperature-time cooling curves for iron compositions of different magnesium content.

From FIG. 4 it may be seen that if the iron solidifies with a graphitic eutectic, as in FIG. 4(a), because there is sufficient magnesium in the sample (and therefore not all neutralised by the sulphur in the cup), then the time taken to cool between the two temperatures is relatively long because the eutectic arrest takes place between them. If, however, the amount of magnesium is not sufficient and it is completely neutralised by the sulphur in the cup, then a carbidic eutectic arrest occurs at a temperature below the lower of the said two temperatures and so a relatively short time between them is recorded.

Assuming the initial temperature was satisfactory, i.e. greater than 1200° C., the control equipment C detects when the temperature falls to 1170° C. and triggers the start of a timer T. Then when the temperature falls to 1135° C. the timer is halted and the elapsed time is recorded and evaluated. If it is greater than a threshold value, say, one minute, this indicates a cooling curve of the kind shown in FIG. 4(a), showing that the eutectic arrest produced graphitic iron on solidification, and a lamp L1 bearing the legend 'PASS' is illuminated. If the elapsed time is less than one minute, indicating that a carbidic eutectic arrest occurred, which in its turn indicates that no residual magnesium was left after neutralisation by the sulphur, this indicating in its turn that the magnesium in the iron was below the threshold value, then a second lamp L2 bearing the legend 'FAIL' is illuminated.

It will be appreciated that the manner of indicating a pass or fail may take any convenient form. Also the control equipment C may be provided with means for manually adjusting the initial threshold temperatures and the upper and lower response temperatures, as well as the time interval, these set values preferably being indicated, for example on LED displays.

In borderline cases, when the magnesium content is only just insufficient, then a mixture of carbidic and graphitic eutectic solidification may occur, known as a mottled structure. When this happens the cooling curve is not arrested until a low temperature has been reached, after which considerable recalescence takes place. In such a case, as shown in FIG. 4(b), the time to cool between the two temperatures is again relatively short and the amount of magnesium is regarded as insufficient to achieve a satisfactory nodular iron structure.

The time of cooling between the two temperatures will depend upon the weight of iron in the thermal analysis cup. A commonly used size of cup produces a sample of about 220 grms. in weight. Such a sample solidifying with a graphitic structure will cool between the two temperatures over a period of around two minutes, whereas for a carbidic or mottled structure in the sample, the time will only be about thirty seconds. In a typical test, therefore, any sample which takes less than about one minute to cool between the two temperatures is concluded to have insufficient magnesium and the batch of iron from which it was taken will have to be rejected or treated with additional magnesium. For samples of other weights, slightly different times would be selected for operating the test and these could readily be determined by carrying out sampling tests. The temperatures which have been selected for timing the test are suitable for irons containing more than about 1.2 per cent of silicon. If for some purpose, however, a lower silicon content is to be used, then the lower temperature of 1135° C. would have to be raised by a few degrees because, as the silicon content falls, the temperature of the carbidic eutectic solidification rises and it is necessary for the lower temperature of the interval to be timed to be above the carbidic eutectic temperature.

It is usual to finally inoculate magnesium-containing cast iron with a silicon-containing inoculant following magnesium treatment and prior to casting. Sometimes this inoculation may be reduced or avoided by the use of a magnesium additive containing a substantial amount of silicon, but on occasions a magnesium alloy free from silicon may be used. The test described in this invention may be carried out using liquid magnesium-containing cast iron which has been inoculated or which has not been inoculated. However, because magnesium itself has a small effect in lowering the graphitic eutectic temperature, if there is a possibility that an unintentionally high magnesium content may have been achieved or if a magnesium alloy has been added which has no inherent inoculating effect, then it is recommended that the test should be carried out after final inoculation of the liquid iron.

If it is necessary to control the retained magnesium content to between upper and lower limits two tests may be made, using two different amounts of sulphur in the thermal analysis cups representing respectively an upper limit and a lower limit of magnesium to be tested for. If both samples solidify with a long cooling time, this indicates that too much magnesium had been added. If the first cup solidifies with a short cooling time and the second one with a long cooling time, this indicates that the magnesium content lies between the two limits intended.

The test is novel in that it uses a combination of sulphur and tellurium in a thermal analysis cup to achieve graphitic solidification as an indication that sufficient magnesium has been added to the iron. In this sense, it differs from any other test previously devised for controlling magnesium content of nodular iron or from tests using tellurium to enable carbon equivalent, carbon content and silicon contents to be determined.

The test can be modified to control the magnesium content of compacted graphite irons, in which case it will be necessary to use two test samples of different sulphur contents, since in a compacted graphite iron there is always a maximum retained magnesium content which may not be exceeded if the iron is not to solidify as a nodular graphite iron, as well as a minimum magnesium content necessary to achieve compacted graphite.

Because the test may be carried out in a period of about two minutes, the result is known sufficiently early often to be able to carry out a second treatment in those cases where the first treatment was insufficient. In such cases, a further addition of magnesium can be made by one of the established methods to the ladle or other treatment vessel.

A simultaneous test may, if required, be carried out for thermal analysis for carbon, silicon and carbon equivalent, using a thermal analysis sample of a conventional type or using one of the earlier inventions for successful measurements to be made on magnesium-treated iron. The present invention when operated with correctly treated nodular iron will only produce a graphitic iron in the thermal analysis cup and measurements made on the cooling curve cannot therefore be used to determine carbon and silicon contents, but only carbon equivalent (liquidus). A second thermal analysis cup would have to be used having been treated according to earlier inventions if carbon and silicon contents were also to be measured by thermal analysis.

We claim:

1. A method of testing the actual magnesium content of magnesium-treated iron wherein a molten sample of the magnesium-treated iron is introduced into a receptacle containing additives of tellurium and either sulphur or selenium and is allowed to cool and solidify, the amounts of tellurium and of said sulphur or selenium being controlled measured quantities, the quantity in the case of tellurium being sufficient to allow carbidic eutectic solidification of non-magnesium-containing iron, the quantity, in the case of the sulphur or selenium, being such that the addition is just sufficient to neutralize a desired content of magnesium in the iron, and then observing whether the cooling behavior results in (1) carbidic eutectic solidification, signifying neutralization of all magnesium in the iron sample such that actual magnesium content is less than the desired magnesium content or (2) graphitic eutectic solidification signifying neutralization of less than all the actual magnesium in the iron sample such that the actual magnesium content is greater than the desired content.

2. The method set forth in claim 1 wherein the presence of graphitic or carbidic eutectic solidification is detected by observing the rate of cooling of said sample through the temperature of eutectic arrest.

3. The method set forth in claim 2 wherein said rate of cooling is detected by measuring the time taken by said sample to cool between first and second predetermined temperatures.

4. The method set forth in claim 3 wherein said first temperature is substantially 1170° C.

5. The method set forth in claim 3 or claim 4 wherein said second temperature is substantially 1135° C.

6. The method set forth in claim 3 wherein the initial temperature of said sample on entering said receptacle is checked and the test is indicated as being void if this initial temperature is below a predetermined value.

7. The method set forth in claim 6 wherein said predetermined value is substantially 1200° C.

8. Test apparatus for determining if the actual content of magnesium is greater or less than a desired content of magnesium in a sample of magnesium-treated iron, comprising a receptacle for the molten magnesium-treated iron sample, said receptacle having a lining which includes predetermined quantities of tellurium and of sulphur or selenium, and temperature-sensing means arranged to produce an electrical output signal indicative of the temperature of the iron sample, the amount of sulphur or selenium being just sufficient to neutralize such desired content of magnesium, the quantity in the case of tellurium being sufficient to allow carbidic eutectic solidification of non-magnesium-containing iron, control equipment to which said signal is fed for detecting the presence of graphitic or carbidic eutectic solidification of the iron sample by monitoring the rate of cooling of the iron sample through the temperature of eutectic arrest, said control equipment including a timer and means for starting said timer when said signal indicates that the iron sample has cooled to a first predetermined temperature and means for detecting the time that has elapsed when said sample has further cooled to a second predetermined temperature, and means for indicating whether such elapsed time is greater or less than a threshold time value, which is mediate the elapsed times required for carbidic and graphitic eutectic solidification, to thereby indicate whether the eutectic solidification is graphitic or carbidic and hence whether the actual magnesium content of the iron is above or below the desired content.

9. The apparatus set forth in claim 8 wherein said control equipment includes means for indicating if the actual initial temperature of the contents of said receptacle is below a desired initial temperature.

* * * * *